(12) United States Patent
Sunohara et al.

(10) Patent No.: US 6,531,150 B1
(45) Date of Patent: Mar. 11, 2003

(54) ENCAPSULATED UNSATURATED FATTY ACID SUBSTANCE AND METHOD FOR PRODUCING THE SAME

(75) Inventors: Hideki Sunohara, Osaka (JP); Ryosei Kamaguchi, Osaka (JP); Toshio Kozaki, Osaka (JP); Masatomo Yoshikado, Osaka (JP); Junko Higuchi, Osakasayama (JP)

(73) Assignee: Morishita Jintan Co., Ltd., Osaka-fu (JP)

( * ) Notice: Subject to any disclaimer, the term of this patent is extended or adjusted under 35 U.S.C. 154(b) by 0 days.

(21) Appl. No.: 09/530,494

(22) PCT Filed: Oct. 26, 1998

(86) PCT No.: PCT/JP98/04819
§ 371 (c)(1),
(2), (4) Date: Jun. 1, 2000

(87) PCT Pub. No.: WO99/22719
PCT Pub. Date: May 14, 1999

(30) Foreign Application Priority Data

Oct. 30, 1997 (JP) ............................... 9-298552

(51) Int. Cl.⁷ ............................ A61K 9/48; A61K 9/64; A61K 9/66; A61K 9/16
(52) U.S. Cl. ....................... 424/463; 424/451; 424/455; 424/456; 424/489; 424/490; 424/491; 424/492
(58) Field of Search .................................. 424/451, 455, 424/456, 463, 489, 490, 491, 492; 428/402.2

(56) References Cited

U.S. PATENT DOCUMENTS

| 4,422,985 A | * | 12/1983 | Morishita et al. ............ 264/4.4 |
| 4,751,241 A | * | 6/1988 | Motoyama et al. .......... 514/532 |
| 4,849,227 A | * | 7/1989 | Cho ........................... 424/498 |
| 5,330,835 A | * | 7/1994 | Kikuchi et al. ........ 428/402.22 |
| 5,362,564 A | * | 11/1994 | Suzuki et al. ............ 428/402.2 |

FOREIGN PATENT DOCUMENTS

| JP | 59-39834 | 3/1984 |
| JP | 64-38019 | 2/1989 |
| JP | 3-52639 | 3/1991 |
| JP | 7-69861 | 3/1995 |

OTHER PUBLICATIONS

H. Bennett, "Concise Chemical and Technical Dictionary", second enlarged edition, p. 395, 1962.*

* cited by examiner

Primary Examiner—Thurman K. Page
Assistant Examiner—S. Tran
(74) Attorney, Agent, or Firm—Merchant & Gould P.C.

(57) ABSTRACT

The present invention relates to an encapsulated unsaturated fatty acid substance in a form of a three-layered capsule, comprising an unsaturated fatty acid or a derivative thereof (11) as a content and a coating layer (10) mainly containing gelatin, encapsulating the content (11), wherein a water-soluble gel layer (12) containing an acid or an acid salt thereof is present between the coating layer (10) and the content (11). The encapsulated unsaturated fatty acid substance of the present invention is characterized by that it has neither insolubility nor deterioration with time, and that it is enteric.

6 Claims, 2 Drawing Sheets

ENCAPSULATED UNSATURATED FATTY ACID SUBSTANCE AND METHOD FOR PRODUCING THE SAME

This application is a 371 of PCT/JP98/04819 filed Oct. 29, 1998.

TECHNICAL FIELD

The present invention relates to an encapsulated unsaturated fatty acid substance. Particularly, the present invention relates to an encapsulated unsaturated fatty acid substance which is enteric and does not deteriorate with time, and a method for producing the encapsulated unsaturated fatty acid substance.

BACKGROUND ART

There have been used water-soluble capsules which encapsulate an oily liquid component and the like in a gelatin containing layer, because they can keep the content isolated from surroundings so as to protect the content, or to eliminate bad odor generating from the content.

Recently, it has been found that an unsaturated fatty acid or its derivative, such as eicosapentaenoic acid (EPA), docosahexaenoic acid (DHA) and the like, has an effect on prevention and cure of hyperlipidemia, and one wishes to take it orally. Since the effective unsaturated fatty acid or derivative thereof has strong odor and it is difficult for us to directly take it, it has been served in a form of a capsule encapsulating it by the gelatin containing layer.

It is known, however, that the capsule encapsulating unsaturated fatty acid or derivative thereof decreases its water-solubility of the gelatin layer as time goes and at last results in insoluble with water. That is believed to cause by a reaction of the unsaturated fatty acid or derivative thereof with gelatin.

In order to prevent the capsule layer containing gelatin from insolubilizing due to the unsaturated fatty acid or derivative thereof, there is proposed a method wherein citric acid is added to gelatin to form a capsule coating layer (as disclosed in Japanese Paten Kokai Publication Sho 59 (1984)-39834), a method wherein a pH of gelatin is adjusted to no more than 5 to form a capsule coating layer (as disclosed in Japanese Paten Kokai Publication Sho 64 (1989)-38019), or the Japanese Paten Kokai Publication Hei 7 (1995)-69861 proposes a method wherein acid or its salt is formulated into a gelatin containing layer to form a capsule containing higher fatty acid or fats, in order to prevent the reaction between gelatin and the content of the capsule.

According to the methods as disclosed in the above-mentioned publications, insolubilization of the gelatin layer is inhibited, but another disadvantage may occur. For example, a part of gelatin layer (particularly, a surface of the layer exposed to air) is brittle and then turns its color to brown to deteriorate the capsule, because gelatin as a film-forming component for the capsule layer is reacted with citric acid or the acid component to be added. In producing the capsule, acid adversely affects and prevents gelatin from gelling to prolong its production period of time. As a result, efficiency of production is poor.

DISCLOSURE OF INVENTION

Accordingly, an object of the present invention is to provide a capsule encapsulating an unsaturated fatty acid or derivative thereof as a content in a gelatin layer, having disadvantages as mentioned above (for example, brittleness, browning and poor efficiency of production of the capsule).

The present invention relates to encapsulated unsaturated fatty acid substance comprising an unsaturated fatty acid or a derivative thereof (11) as a content and a coating layer (10) mainly containing gelatin, encapsulating the content (11), wherein a water-soluble gel layer (12) containing an acid or an acid salt thereof is present between the coating layer (10) and the content (11).

The present invention further provides a method for producing the encapsulated unsaturated fatty acid substance, comprising simultaneously extruding three components from three nozzles into a cooling solution, wherein the first component is an unsaturated fatty acid or a derivative thereof (4) and is extruded from the first nozzle (1), the second component is an acid or an acid salt thereof (5) and is extruded from the second nozzle (2), the third component is a capsule coating material mainly containing gelatin (6) and is extruded from the third nozzle (3), and the first nozzle (1), second nozzle (2) and third nozzle (3) are arranged concentrically and their diameters gradually increase in a numerical order.

BEST MODE FOR CARRYING OUT THE INVENTION

The present invention will explain briefly as follows.

Capsule

FIG. 1 schematically shows a cross-sectional view of a capsule (20) of the present invention, encapsulating an unsaturated fatty acid or derivative thereof as a content (11) with a coating layer (10) mainly containing gelatin. In FIG. 1, number "10" indicates the coating layer, "11" indicates the content and "12" indicates a water-soluble gel layer containing acid or acid salt thereof.

Coating Layer

A material for forming the coating layer (10) of the capsule (20) according to the present invention generally formed from gelatin, and if desired, another material such as a protein except gelatin, or a polysaccharide (for example, albumin, pectin, guaran gum, carrageenan, agar and the like) may be contained. When the material for forming the coating layer contains protein or polysaccharide, it may be contained in an amount of 100 parts by weight to one part by weight, preferably 67 parts by weight to one part by weight, based on 100 parts by weight of gelatin being its base material.

The coating layer (10) may contain an additive, for example an enteric material, a plasticizer, a preservative and a colorant and the like, in addition to gelatin and the materials mentioned above.

A suitable example of the enteric material used in the present invention is pectin, alginic acid, cellulose such as carboxyl methylcellulose, celluloseacetate phthalate, and the like, Eudragit® which is one of an acrylic copolymer, and the like, but these are not limitative examples. Preferred is pectin as the enteric material. The addition of the enteric material into the material for forming the coating layer (10) makes the capsule (20) is enteric and therefore the capsule does not dissolve in stomach when oral administration of it. As the result, so-called "returned odor" (that is, pleasant odor or fishy-smelling odor returned from a stomach to an oral cavity generated from fish oil and the like present in the content of the capsules by the dissolution of the capsule in stomach would disappear, and therefore, the product quality increases.

The plasticizer may include polyhydric alcohols, such as sorbitol, glycerin, polyethylene glycol and the like. In the present invention, examples of the suitable preservative and colorant are known in the art and include benzoic acid, para-oxybenzoate, caramel colorant, gardenia colorant, carotene colorant, tar colorant and the like.

A total amount of the additives may be two parts by weight to 98 parts by weight, based on 100 parts by weight of gelatin in the coating layer. Particularly, the enteric material may be contained in an amount of two parts by weight to 98 parts by weight, based on 100 parts by weight of gelatin.

In order to inhibit oxygen-permeability of the capsule of the present invention, sucrose may be contained in the coating layer, in addition to the film-forming material and additives. When sucrose is not contained in the coating layer, oxygen may permeate through the water-soluble gel layer (12) to reach the content and oxidize the unsaturated fatty acid and derivative thereof (11) during a long storage period of time. Oxidized unsaturated fatty acid and derivative thereof increase peroxide value (POV) and deteriorate product quality. Sucrose efficiently inhibits the disadvantage. Sucrose may be contained in an amount of one part by weight to 100 parts by weight based on 100 parts by weight of gelatin.

Water-soluble Gel Layer

The capsule (20) of the present invention contains the water-soluble gel layer (12) between the coating layer (10) and the content (12). An example of a material used for forming the water-soluble gel layer (12) includes protein or polysaccharide as a film-forming material which has been hitherto used for production of the capsule, such as gelatin, pectin, guaran gum, carrageenan, agar and the like.

The water-soluble gel layer (12) also contains an acid or an acid salt thereof, in addition to the film-forming material, to prevent the capsule from insolubilizing with time.

An example of the acid or acid salt thereof suitably used in the water-soluble gel layer (12) is a water-soluble organic acid, an inorganic acid, or an acid salt thereof (for example, sodium salt). A suitable organic acid is one having 2 to 6 carbon atoms, including, for example, citric acid, malic acid, tartar acid, fumaric acid, lactic acid, butyric acid, succinic acid and the like, an acid salt thereof (for example, sodium malate, potassium succinate, calcium citrate and the like); or a mixture thereof. An example of inorganic acid includes phosphoric acid, polyphosphoric acid, carbonic acid, an acid salt thereof (for example, dibasic sodium phosphate) or a mixture thereof.

In the capsule (20) of the present invention, the water-soluble gel layer (12) may also contain the enteric material, the plasticizer and the colorant and the like as those described in the explanation of the coating layer, in addition to the film-forming material and the acid or acid salt thereof.

An amount of the acid or acid salt thereof added to the water-soluble gel layer (12) is generally 0.01 to 50% by weight, preferably 0.05 to 20% by weight, based on 100% by weight of a gel formed from the film-forming material. When the amount is less than 0.01% by weight, it is impossible to inhibit the insolubilization of the capsule. When the amount is above 50% by weight, gelling power of the material decreases, and therefore, formation of the layer is not achieved.

In the present invention, both the film-forming material for the coating layer (10) (containing the additives) and the material for the water-soluble gel layer (12) may be preferably prepared in a form of a solution by adding water and heating when producing the capsule.

Content

The content (11) encapsulated in the capsule of the present invention is an unsaturated fatty acid or a derivative thereof. An example of suitable unsaturated fatty acid includes fish oil and a purified material thereof, and may be selected from the group consisting of liver oil, eicosapentaenoic acid (EPA), docosahexaenoic acid (DHA), arachidonic acid, prostaglandin, a derivative thereof (for example, ester, salt, amide and the like), and a mixture thereof.

The content of the capsule according to the present invention may also contain various types of a stabilizer for unsaturated fatty acid or a derivative thereof (such as antioxidant, vitamin E, vitamin C, β-carotene, wheat germ oil and the like), together with the unsaturated fatty acid or derivative thereof.

An amount of the content encapsulated in the capsule of the present invention is generally 10% by weight to 95% by weight, preferably 40% by weight to 90% by weight, based on the total weight of the capsule.

Method for Producing Capsule

A method for producing the encapsulated unsaturated fatty acid substance may be a conventional method for producing a soft capsule. An example of the method for producing the capsule includes a method containing steps of preparing a sheet for the coating layer mainly containing gelatin and a sheet for the water-soluble gel layer containing an acid or an acid salt thereof, respectively, laminating both sheets, drying to obtain a dried sheet and encapsulating unsaturated fatty acid or the derivative thereof as the content with the dried sheet on a rotary filler to form a seamed capsule; and another method for producing a seamless capsule by using an instrument equipped with some nozzles arranged concentrically.

In order to produce the encapsulated unsaturated fatty acid substance of the present invention, the latter method for producing a seamless capsule using some nozzles arranged concentrically, particularly a triplet nozzle arranged concentrically, is more preferable. The method is described, for example, in Japanese Patent Kokai Publication Hei 3 (1991)-52639 and in Japanese Patent No. 2806564. In the method using the triplet nozzle arranged concentrically, the content (4) is extruded through an inner nozzle (1), the material for forming the water-soluble gel layer (5) is extruded through an intermediate nozzle (2) and a film-forming material for a coating layer (6) is extruded through an outer nozzle (3), simultaneously, into a cooling oil to continuously mold a capsule in a form of a triplet structure. One example of the method for producing the seamless capsule generally used in the present invention is shown in FIG. 2.

FIG. 2 schematically shows a cross-sectional view of one embodiment of a nozzle portion equipped in a machine suitably used in the method for producing the encapsulated unsaturated fatty acid substance in a form of the seamless capsule according to the present invention. In FIG. 2, the unsaturated fatty acid (4) as the content of the capsule supplied to the nozzles is extruded from an annular end of an inner nozzle (called the first nozzle) (1), the material for forming the water-soluble gel layer (5) is extruded from an annular end of an intermediate nozzle (called the second nozzle) (2) and a film-forming material for a coating layer (6) is extruded from an annular end of an outer nozzle (called the third nozzle) (3), simultaneously, to make a three-phase composite jet stream, followed by releasing the jet stream into a cooling solution (8) to obtain the encapsulated unsaturated fatty acid substance (7) of the present invention in a form of the seamless capsule.

In the method of the present invention, since all of the loading materials are liquid, the encapsulation process can be easily performed by adequately vibrating the jet stream with a vibration means to readily release the jet stream, and thereby a particle size of the resulting capsules may be controlled uniformly. The capsule of the present invention may be formed into a desirable particle size of 0.1 mm to 20 mm, preferably 0.3 to 8 mm.

The encapsulated unsaturated fatty acid substance (7) produced by the method of the present invention may be used in any way of an undried form remaining moisture in the coating layer, or a dried form.

The water-soluble gel layer (12) in the capsule of the present invention has a thickness of 0.001 to 5.00 mm, preferably 0.01 to one mm.

EXAMPLES

The following Examples further illustrate the present invention in detail but are not to be construed to limit the scope thereto.

Example 1

The formulations as shown in Table 1 were mixed to prepare a film-forming material for a coating layer, a solution for forming a water-soluble gel layer and unsaturated fatty acid as a content, respectively. Each material was extruded through each one of the triplet nozzle arranged concentrically and released into a cooling solution (a vegetable oil) to produce capsules in a form of a triplet structure.

Examples 2 and 3 and Comparative Examples 1 to 3

In Examples and Comparative Examples, capsules in a form of a triplet structure were produced in the same way as described in Example 1, except that a film-forming material for a coating layer, a solution for forming a water-soluble gel layer and unsaturated fatty acid as a content were prepared by using the formulations as shown in Table 1.

TABLE 1

| | | (Amount: Parts by weight) | | | | | |
|---|---|---|---|---|---|---|---|
| | | Examples | | | Comparative Examples | | |
| Formulations | | 1 | 2 | 3 | 1 | 2 | 3 |
| Film-forming solution for coating layer (30%) | Gelatin | 75.0 | 71.0 | 83.0 | 75.0 | 75.0 | 80.0 |
| | Sucrose | 20.0 | 20.0 | 15.0 | 20.0 | | |
| | Pectin | 5.0 | 8.0 | | 5.0 | 5.0 | |
| | Methyl paraben | | 1.0 | 1.0 | | | |
| | Gardenia colorant | | | 1.0 | | | |
| | Glycerin | | | | | 20.0 | |
| | Sorbitol | | | | | | 20.0 |
| Solution for forming a water-soluble gel layer (20%) | Gelatin | 95.0 | 92.0 | 95.0 | 80.0 | 80.0 | 80.0 |
| | Citric acid | 5.0 | 8.0 | | | | |
| | Malic acid | | | 5.0 | | | |
| | Glycerin | | | | 20.0 | 20.0 | 20.0 |
| Content (50%) | EPA | 99.4 | 99.0 | | 99.4 | 99.0 | 99.4 |
| | Vitamin E | 0.3 | 1.0 | 0.5 | 0.3 | 1.0 | 0.5 |
| | Lecithin | 0.1 | | 0.1 | 0.1 | | 0.1 |
| | Lemon oil | 0.2 | | | 0.2 | | |
| | DHA | | | 99.4 | | | |

Procedure of Evaluation (1) Test for Stability with Time

100 Grams of capsules obtained in Examples 1 to 3 and Comparative Example 1 to 3 was put in a sealable container and held at a temperature of 40° C. for 6. Then, a test for a change of stability of with time (that is a change of POV of an unsaturated fatty acid and derivative thereof contained in the coating layer) was conducted at initial and after one, two, three, four and six months. The results are shown in Table 2.

(2) Test for Change of Solubility Rate with Time

The capsules were held in the same way as described in the above test (1) and evaluated for a change of solubility rate with time at initial and after one, two, three, four and six months, according to the procedure of decay test, in 13th Pharmacopeia of Japan. The results are shown in Table 3.

TABLE 2

(1) Results of test for a change of stability with time
(Results for measuring a change of POV)
[At 40° C.; milliequivalent/kg]

| | After (month) | | | | | |
|---|---|---|---|---|---|---|
| | Initial | 1 | 2 | 3 | 4 | 6 |
| Examples | | | | | | |
| 1 | 4.5 | 4.2 | 4.4 | 3.8 | 3.4 | 3.0 |
| 2 | 2.5 | 2.4 | 2.0 | 1.8 | 1.6 | 1.0 |
| 3 | 2.6 | 2.3 | 3.1 | 3.6 | 4.1 | 4.5 |
| Comparative Examples | | | | | | |
| 1 | 4.2 | 4.0 | 4.0 | 3.5 | 3.6 | 3.2 |
| 2 | 2.3 | 2.2 | 2.8 | 6.3 | 11.0 | 15.2 |
| 3 | 3.0 | 4.6 | 4.9 | 6.9 | 10.1 | 12.6 |

TABLE 3

(2) Results of test for a change of solubility rate with time
[At 40° C.; minute (') and second (")]

| | After (month) | | | | | |
|---|---|---|---|---|---|---|
| | Initial | 1 | 2 | 3 | 4 | 6 |
| Examples | | | | | | |
| 1 | 4'05" | 3'50" | 5'40" | 6'12" | 7'30" | 7'50" |
| 2 | 3'08" | 3'13" | 3'30" | 3'30" | 3'50" | 3'50" |
| 3 | 3'28" | 3'40" | 4'24" | 4'54" | 5'30" | 6'30" |
| Comparative Examples | | | | | | |
| 1 | 4'11" | 7'42" | 14'40" | insoluble | | |
| 2 | 3'15" | 8'54" | insoluble | | | |
| 3 | 3'32" | 4'20" | 6'50" | 18'30" | insoluble | |

It is found from results as shown in Tables 2 and 3 that Examples 1 to 3 (capsules of the present invention) exhibit neither delay of time to dissolve the capsules with time nor deterioration thereof.

On the other hand, significant decrease of solubility rate, the increase of POV and the insolubility phenomenon due to the deterioration of the capsules were found in the results for capsules of Comparative Examples 1 to 3 formulated in the conventional way, as shown in Table 2 and 3.

Effects of Invention (1) The capsule (20) of the present invention has a structure in which the content of an unsaturated fatty acid or derivative thereof (11) is encapsulated by the water-soluble gel layer (12) containing the acid (particularly, citric acid), and then covered with the coating layer (10) mainly containing gelatin. In the structure, the disadvantages generating in the water-soluble gel layer (12) by the addition of citric acid (for example, brittleness and browning) may be effectively prevented by covering and protecting the water-soluble gel layer (12) with the coating layer (10). Since the water-soluble gel layer (12) is reinforced by covering the outside of the water-soluble gel layer (12) with the coating layer (10), even if a gelation time of the water-soluble gel layer (12) is elongated, a period of time to produce the capsules is controlled by the gelation time of the coating layer (10) containing gelatin. Therefore, efficiency of production of the capsule may be improved.

The method for producing a capsule of the present invention may achieve both mass production and increase efficiency of production by using a concentrical multi-nozzle.

(2) Formulating sucrose to the coating layer (10) containing gelatin as the most-outer coating of the capsule may inhibit oxygen-permeability of the capsule, and also efficiently prevent the oxidation and the deterioration of the unsaturated fatty acid and derivative thereof induced by permeating oxygen into the capsule.

Making the coating layer (10) enteric eliminates the fetid "returned odor" generating by the dissolution of the capsule in stomach, and also maintains effects of orally administering the unsaturated fatty acid and derivative thereof, particularly EPA and DHA because of easy dissolution of the capsule in intestine.

(3) The capsule of the present invention having the triplet structure composed of the water-soluble gel layer, encapsulating the content, covered with the gelatin-containing coating layer as the most-outer layer may provide many functions which had not been achieved by a conventional capsule. Thus, the capsule of the present invention significantly improves the quality of product containing the unsaturated fatty acid and the derivative thereof. Further, the capsule having the triplet structure of the present invention may eliminate all disadvantages which had been generated in the conventional double structure.

Figure 1:
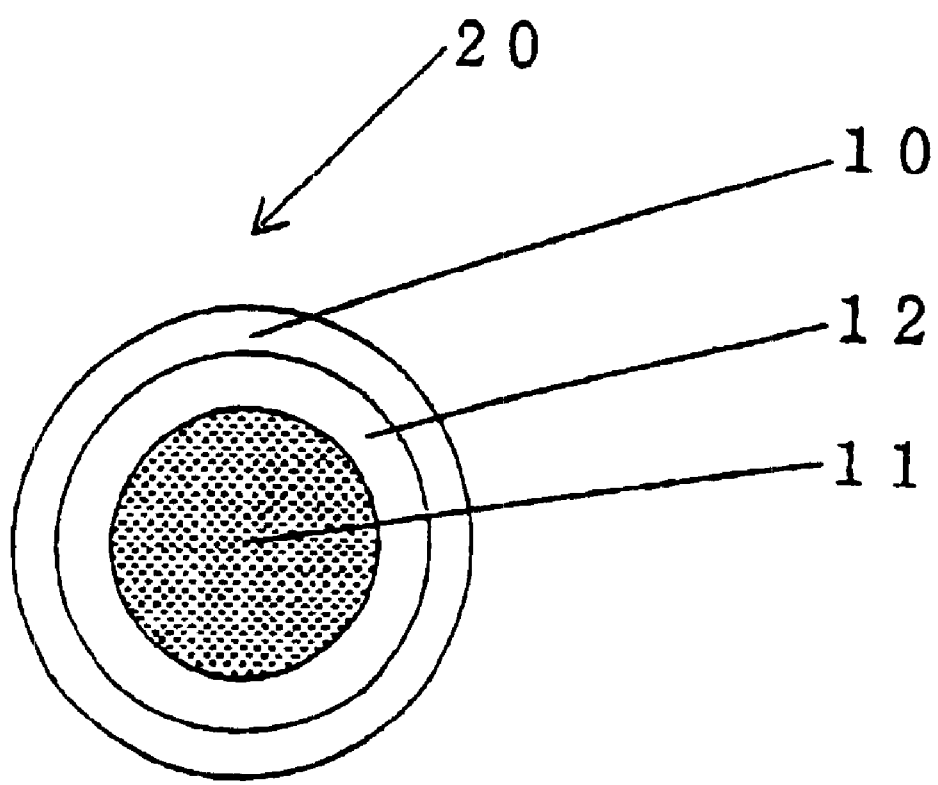
FIG. 1 schematically shows a cross-sectional view of the encapsulated unsaturated fatty acid substance (20) of the present invention.
Figure 2:
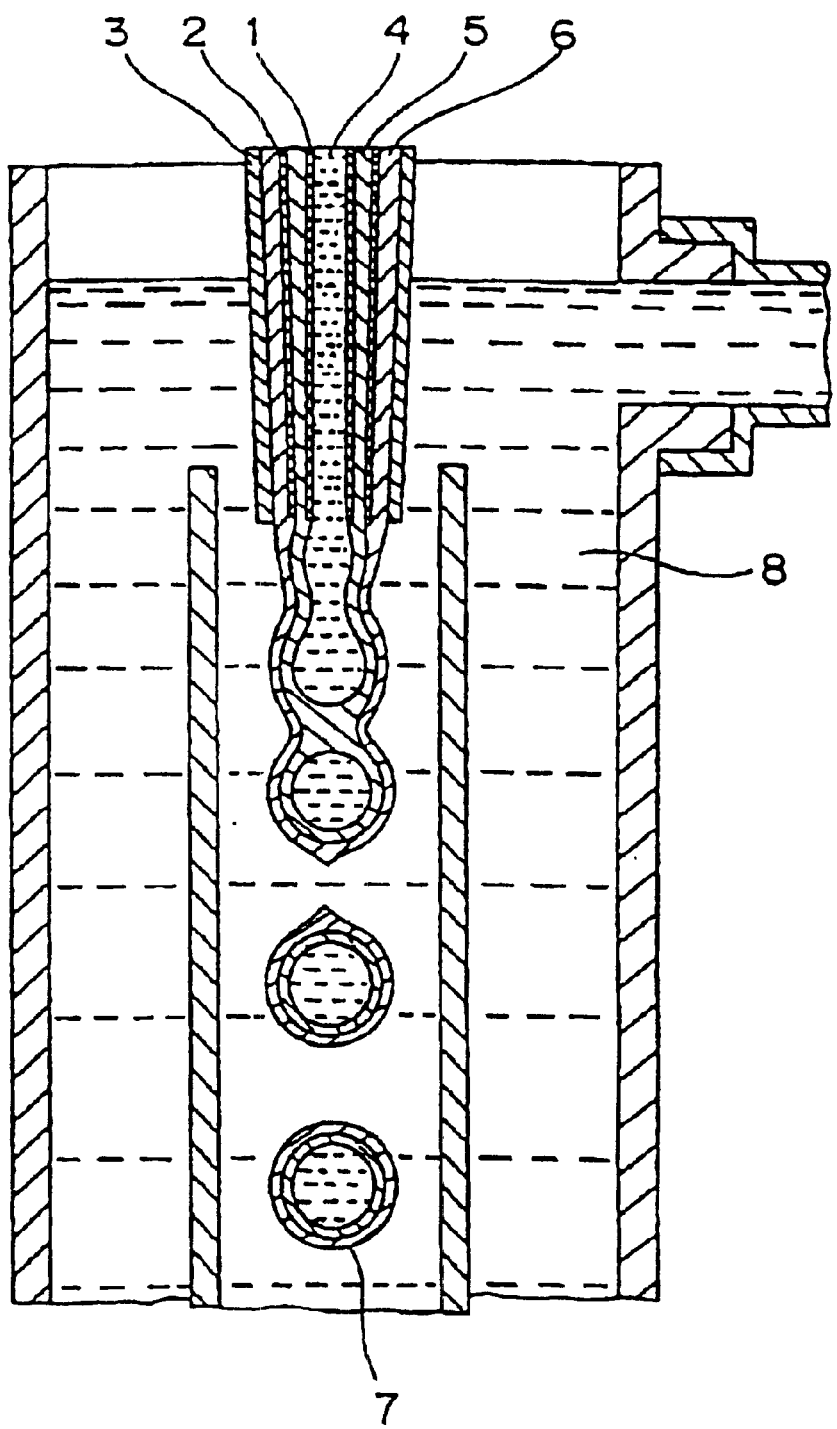
FIG. 2 schematically shows a cross-sectional view of one embodiment of a nozzle portion in a machine for producing the encapsulated unsaturated fatty acid substance in a form of the seamless capsule according to the present invention.

What is claimed is:

1. An encapsulated unsaturated fatty acid substance comprising an unsaturated fatty acid or a derivative thereof as a content and a coating layer mainly containing gelatin, encapsulating the content, wherein a water-soluble gel layer containing an acid or an acid salt thereof is present between the coating layer and the content; and wherein the capsule has a particle size of 0.1 to 20 mm.

2. The encapsulated unsaturated fatty acid substance according to claim 1, wherein the coating layer contains sucrose.

3. The encapsulated unsaturated fatty acid substance according to claim 1, wherein the coating layer is enteric.

4. The encapsulated unsaturated fatty acid substance according to claim 1, wherein the unsaturated fatty acid or derivative thereof is selected from the group consisting of liver oil, eicosapentaenoic acid (EPA), docosahexaenoic acid (DHA), an ester, salt, amide thereof, and a mixture thereof.

5. The encapsulated unsaturated fatty acid substance according to claim 1, wherein the water-soluble gel layer has a thickness of 0.001 to 5.0 mm.

6. A method for producing the encapsulated unsaturated fatty acid substance according to claim 1, comprising simultaneously extruding three components from three nozzles into a cooling solution, wherein the first component is an unsaturated fatty acid or a derivative thereof and is extruded through the first nozzle, the second component is an acid or an acid salt thereof and is extruded through the second nozzle, the third component is a capsule coating material mainly containing gelatin and is extruded through the third nozzle, and the first nozzle, second nozzle and third nozzle are arranged concentrically and their diameters gradually increase in a numerical order.

* * * * *